(12) United States Patent
Smirles et al.

(10) Patent No.: US 7,801,605 B2
(45) Date of Patent: Sep. 21, 2010

(54) DISPOSABLE DEFIBRILLATOR ELECTRODE ASSEMBLY

(75) Inventors: William J. Smirles, Deerfield, IL (US); Johnny Houston Anderson, Hollywood (GB)

(73) Assignee: Heartsine Technologies Limited, Belfast (GB)

( * ) Notice: Subject to any disclaimer, the term of this patent is extended or adjusted under 35 U.S.C. 154(b) by 1042 days.

(21) Appl. No.: 10/542,314

(22) PCT Filed: Jan. 15, 2004

(86) PCT No.: PCT/EP2004/000402

§ 371 (c)(1),
(2), (4) Date: Jul. 15, 2005

(87) PCT Pub. No.: WO2004/064919

PCT Pub. Date: Aug. 5, 2004

(65) Prior Publication Data

US 2006/0058846 A1    Mar. 16, 2006

(30) Foreign Application Priority Data

Jan. 17, 2003    (IE)    ................................ S20030023

(51) Int. Cl.
*A61N 1/39*    (2006.01)

(52) U.S. Cl. .............................................. 607/5; 607/4

(58) Field of Classification Search .................... 607/4, 607/5
See application file for complete search history.

(56) References Cited

U.S. PATENT DOCUMENTS

| | | | | |
|---|---|---|---|---|
| 5,591,213 | A * | 1/1997 | Morgan | 607/5 |
| 6,029,085 | A * | 2/2000 | Olson et al. | 607/5 |
| 6,125,298 | A * | 9/2000 | Olson et al. | 607/5 |
| 6,148,233 | A * | 11/2000 | Owen et al. | 607/5 |
| 6,427,083 | B1 * | 7/2002 | Owen et al. | 607/5 |
| 6,556,864 | B1 * | 4/2003 | Picardo et al. | 607/5 |
| 6,611,709 | B2 * | 8/2003 | Faller et al. | 607/5 |
| 6,662,046 | B2 * | 12/2003 | Hansen | 607/5 |
| 2003/0065363 | A1 * | 4/2003 | Faller et al. | 607/5 |
| 2004/0111122 | A1 * | 6/2004 | Daynes et al. | 607/5 |
| 2004/0162586 | A1 * | 8/2004 | Covey et al. | 607/5 |

* cited by examiner

*Primary Examiner*—Carl H Layno
*Assistant Examiner*—Joseph Stoklosa
(74) *Attorney, Agent, or Firm*—Porter, Wright, Morris & Arthur, LLP

(57) ABSTRACT

A disposable electrode assembly for a portable defibrillator (12) comprises defibrillator electrodes (14), batteries (24) for powering the defibrillator, and a connector (22) for connecting the electrodes and batteries to the defibrillator. The connector has power output terminals (20) for connecting the battery to the defibrillator and high voltage input terminals (20) for applying a defibrillation voltage to the electrodes. The batteries (24) are housed in the connector (22) or mounted on the rear of one electrode.

5 Claims, 16 Drawing Sheets

DISPOSABLE DEFIBRILLATOR ELECTRODE ASSEMBLY

This invention relates to a disposable electrode assembly for a portable defibrillator.

Portable defibrillators have been available for the last 20 years. The operation of these devices has always involved, at minimum, three actions: step (1) applying a power source to the device (either through a battery pack or a mains plug); step (2) plugging a set of defibrillation electrodes (pads) into the device and applying the electrodes to the patient's bare chest, and step (3) turning the device on (either via an on/off button or opening a lid, etc.).

In a public situation, e.g. a railway station, airport or the like, it is desirable that the device be operable by a lay member of the public without undue complication.

Accordingly, it is an object of the invention to simplify the operation of a portable defibrillator, at least to the extent that steps (1) and (2) above are combined.

According to an aspect of the present invention, there is provided a disposable electrode assembly as specified in claim 1.

The invention further provides a combination of a defibrillator and a disposable electrode assembly as specified in claim 7.

It is a subsidiary object of the invention also to eliminate step (3) above, so that a single action will power the defibrillator and turn it on.

A subsidiary benefit of the invention is that in conventional defibrillation using disposable pads and batteries, battery management must be carefully considered and constantly monitored. The present invention separates the process of battery management from the defibrillation process by incorporating the power source for the defibrillator within the disposable electrode assembly.

The invention is also directed to a method by which the described apparatus operates and including method steps for carrying out every function of the apparatus.

The invention will be understood in greater detail from the following description of preferred embodiments thereof given by way of example only and with reference to the accompanying drawings, in which.

In the drawings, the same or equivalent components have the same reference numerals.

Figure 1:
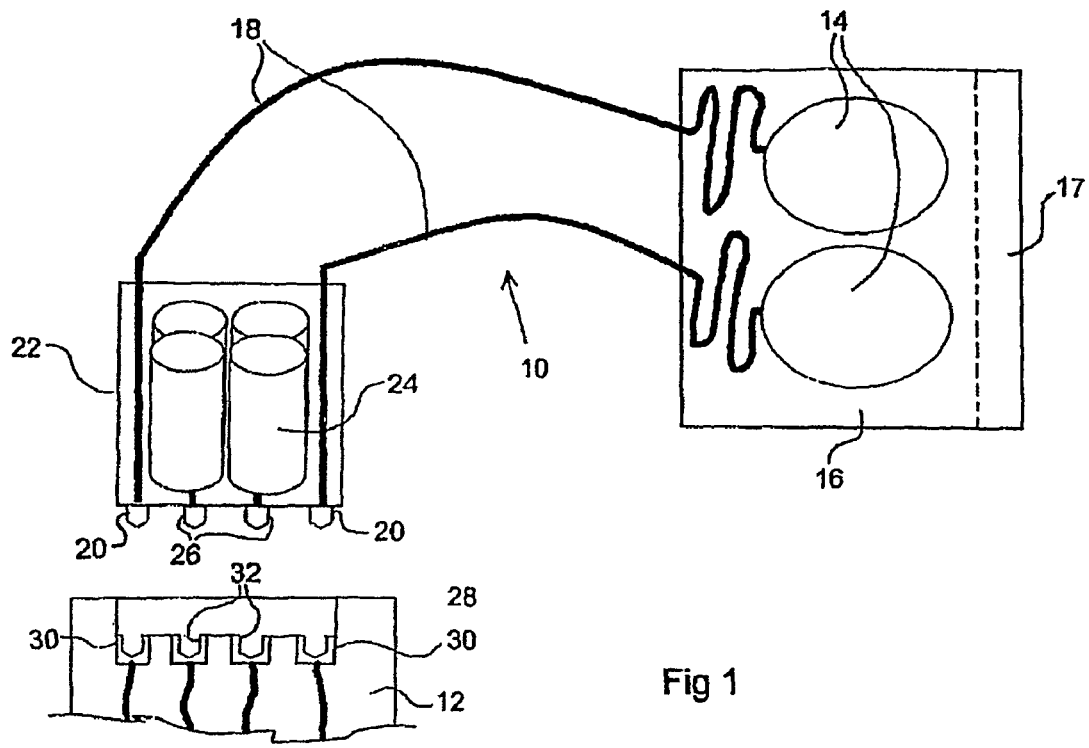
FIG. 1 is a schematic diagram of a first embodiment of the invention.

Referring to FIG. 1, a first embodiment of disposable electrode assembly 10 for a portable defibrillator 12 comprises a pair of defibrillation electrodes (hereafter referred to simply as "pads") 14 hermetically sealed in a pouch 16 from which they may be removed for use by removing a "tear-off" strip 17. Flexible electrically conductive leads 18 connect the pads 14 to respective ones of a pair of outer terminals 20 of a connector 22. The connector 22 also houses a set of batteries 24 which are connected in series across a pair of inner terminals 26 of the connector 22.

In use the connector 22 is plugged into a complementary connector 28 of the defibrillator 12. The complementary connector 28 has a pair of outer terminals 30 which are engaged by the terminals 20 of the connector 22, and a pair of inner terminals 32 which are engaged by the terminals 26 of the connector 22. Thus, the terminals 26 of the connector 22 are power output terminals which in use supply power to the defibrillator 12 via the terminals 32, while the terminals 20 of the connector 22 are high voltage input terminals which receive from the defibrillator 12, via the terminals 30, a defibrillation voltage for application to the pads 14.

The defibrillator 12 may be turned on automatically by insertion of the connector 22 into the connector 28, or it may be turned on by some further action as will be described. In any event, save for the location of the batteries in the connector 22, in all other respects the defibrillator may be entirely conventional.

Figure 2:
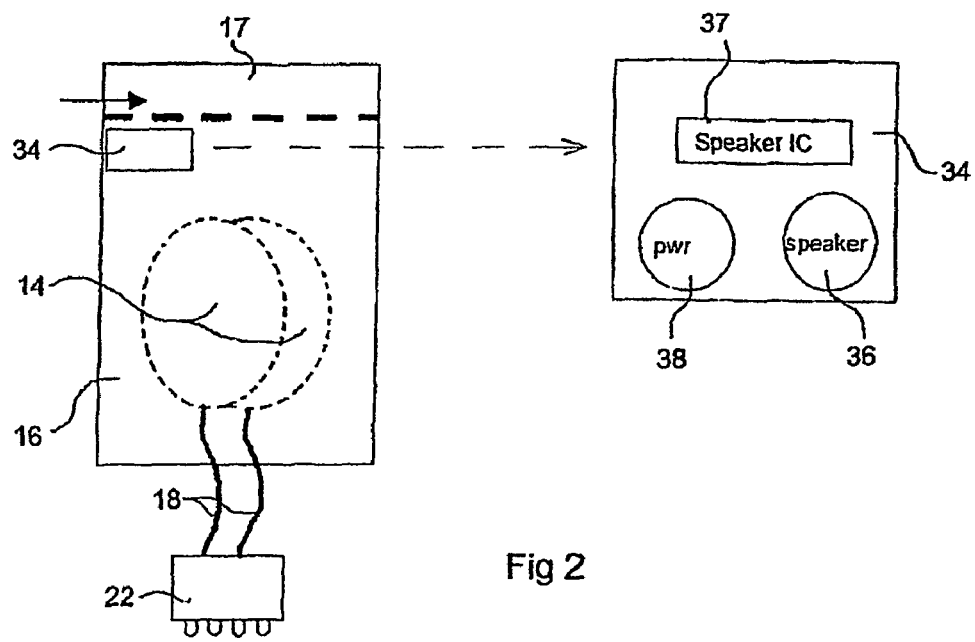
FIG. 2 shows a modification of the embodiment of FIG. 1.

FIG. 2 shows a modification to FIG. 1, where the pouch 16 contains a voice module 34 comprising a speaker 36, a speaker IC 37, and its own power cell 38. This is activated upon removing the tear-off strip 17 to give spoken instructions to the lay user how to plug in the connector 22 from which point the defibrillator itself shall take over the operation. Voice modules 34 are well known and used, for example, in the novelty greetings card industry.

Figure 3:
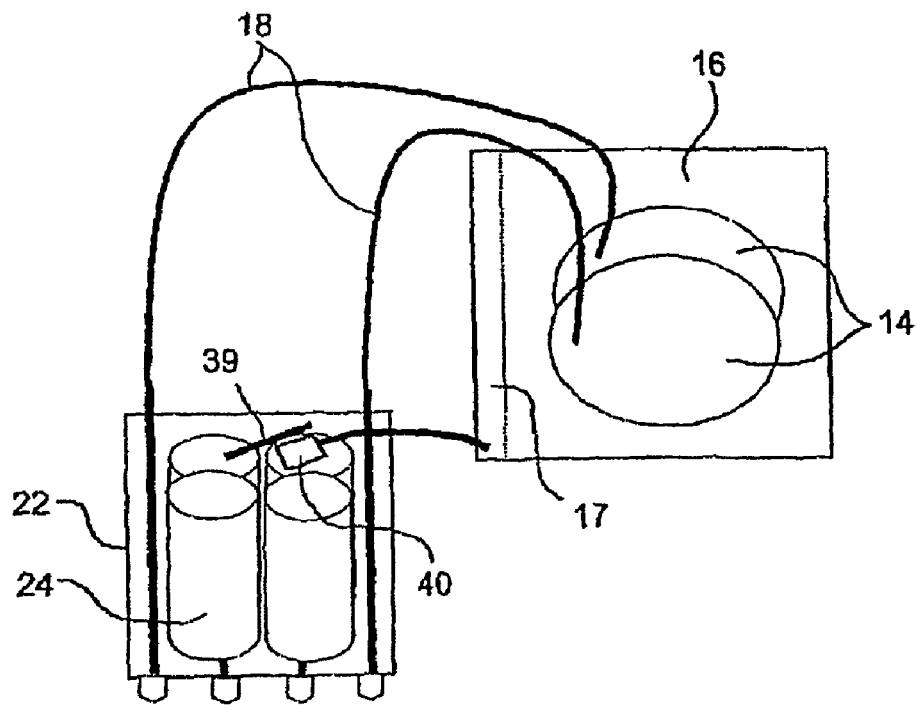
FIGS. 3 to 9 are schematic diagrams of further embodiments of the invention.

In another embodiment, FIG. 3, the power supply circuit which connects the batteries 24 in series within the connector 22 includes a spring biased contact 39. This is biased towards a counter contact (not shown) but is maintained out of engagement with such counter contact by an insulating tab 40 interposed between the two. Removal of the tear-off strip 17 to open the pouch 16 pulls the tab 40 from under the contact 39, allowing it to engage its counter contact and thus automatically complete the power supply circuit within the connector 22.

Figure 4:
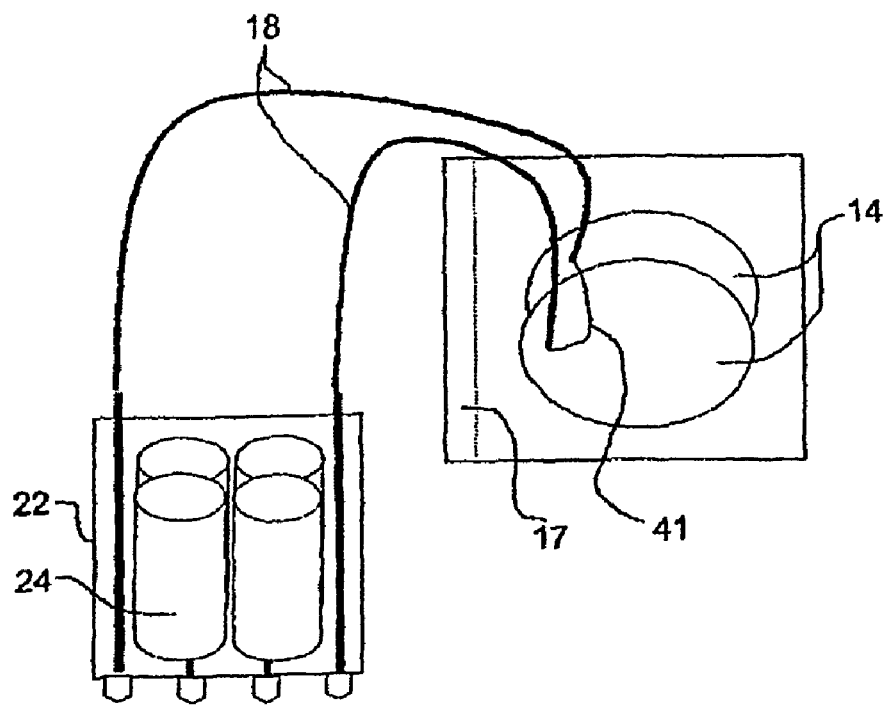

A variation of this includes means for sensing when the pads 14 are separated, FIG. 4, by low power monitoring circuitry internal to the defibrillator 12 which checks to see if an electrical connection 41 between the pads 14 has been broken. The defibrillator 12 turns itself on when the connection 41 is sensed as broken, meaning that the pads 14 have been removed from the pouch 16 and separated. One way of doing this is shown in the circuit diagram of FIG. 4A.

The pads 14, here individually referenced 14A and 14B to distinguish one from the other, are mounted on a release liner 15 within the pouch 16 (not shown). The connection 41, having a resistance R3, is also mounted on the liner 15 and creates an electrical link between the two pads 14A and 14B.

As described, the pads 14A and 14B are attached to the connector 22 containing the batteries 24 which supply a voltage $V_{batt}$.

Figure 4A:
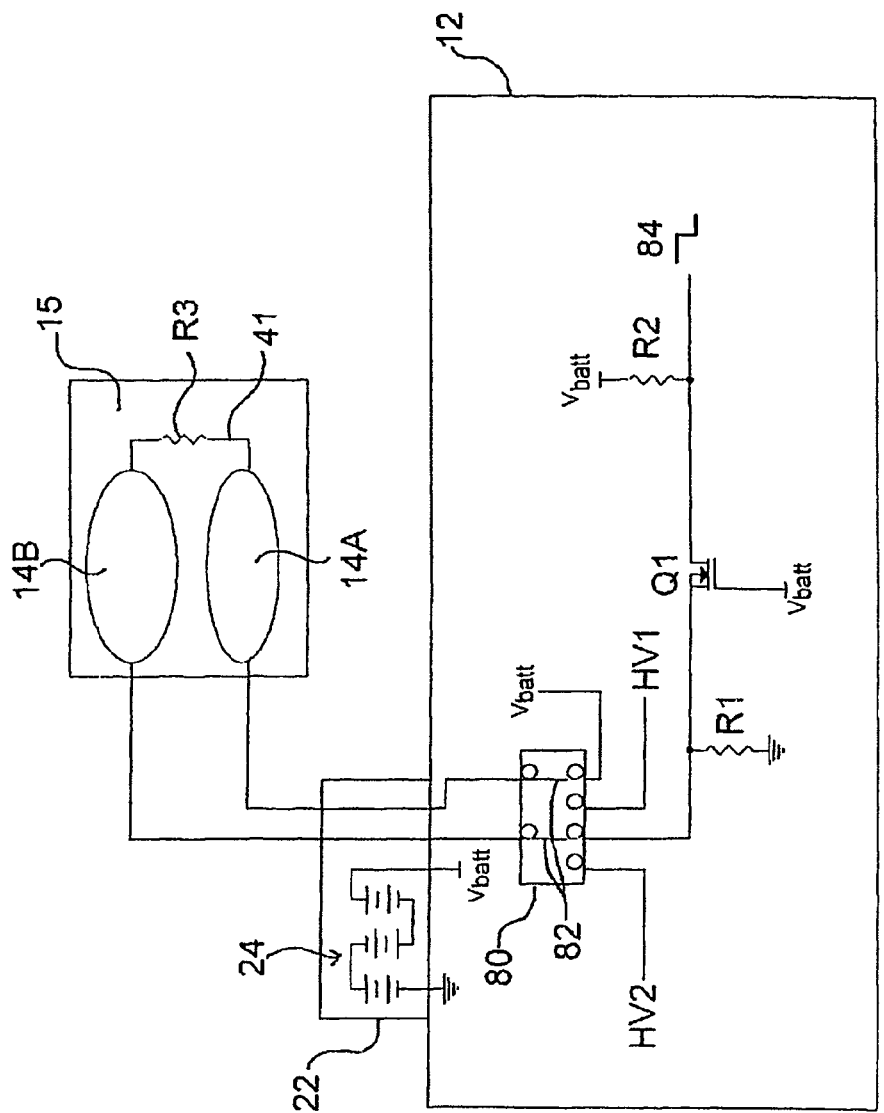

When the connector 22 is plugged into the defibrillator 12 the pads 14A and 14B are connected to a changeover unit 80 (such as a relay) having changeover contacts 82. Initially, as seen in FIG. 4A, the changeover contacts 82 connect the pad 14A to $V_{batt}$ and the pad 14B to ground via a resistor R1 and to the source of an FET Q1. This forms a circuit in which the source of Q1 is pulled up to $V_{batt}$ via R3, resistor R1 being sufficiently large that current drain from $V_{batt}$ and the pull down effect with respect to R3 is minimised. $V_{batt}$ is also be applied to the gate of Q1 and to a resistor R2 pulling up the drain of Q1. Resistor R2 is sufficiently large that current drain from $V_{batt}$ is minimised. This state is maintained as long as the pads 14 remain attached to the release liner 15.

To turn the defibrillator on, either or both pads 14 are removed from the release liner 15. This breaks the circuit formed by R3 which pulled the source of Q1 to $V_{batt}$, so that the source of Q1 is now pulled to ground via R1. This turns on Q1 and in doing so pulls down the voltage at the drain of Q1 to a value determined by the divider created by R2 and R1. This voltage drop 84 is detected by the defibrillator control circuitry (not shown) which responds by switching over the contacts 82 to connect the pads 14A and 14B to respective high voltage terminals HV1 and HV2 within the defibrillator.

The embodiments of FIGS. 3 and 4 assume that the connector 22 is, in use, already plugged into the defibrillator 12, so the battery power is only required to be applied when the pads are actually deployed for use. This contrasts with the embodiment of FIG. 1 where it is assumed that the connector 22 is not pre-connected to the defibrillator 12, so that the mere act of plugging it in can apply power and turn the defibrillator on.

Figure 5:
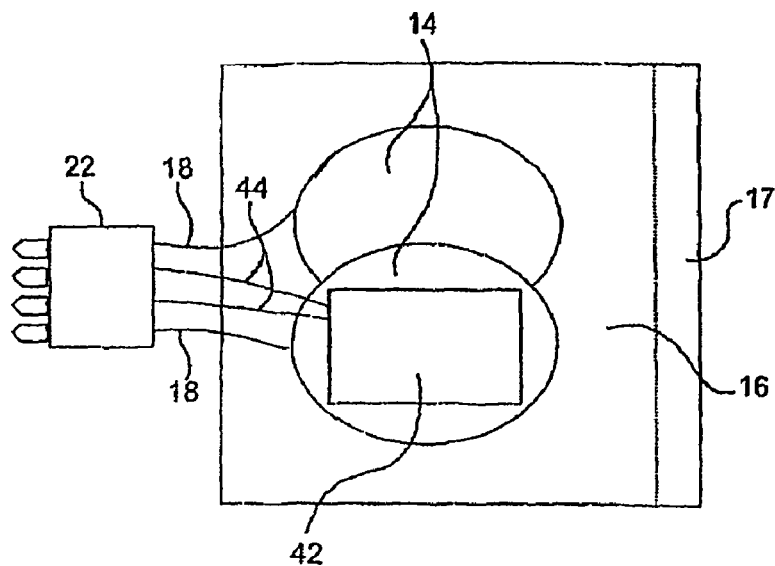
Figure 6:
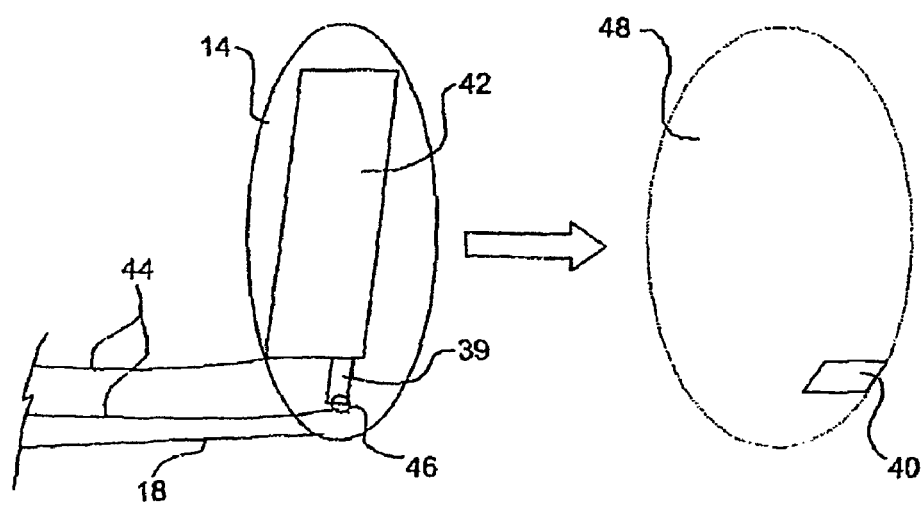

In the embodiment of FIG. 5 the batteries are not housed in the connector 22 but instead a flat battery pack 42 is mounted on the rear of one or both pads 14. This requires extra wires 44 to the connector 22 to carry the power. As shown in FIG. 6, and similar to the embodiment of FIG. 3, the power supply circuit may include a spring contact 39 biased against a counter contact 46 but normally held electrically disconnected therefrom by an insulating tab 40. The tab 40 is fixed to a release liner 48 such that, when the liner 48 is on the pad 14, the tab 40 is interposed between the contacts 39 and 46. However, when the liner 48 is removed from the pad 14 the tab 40 is withdrawn from between the contacts 39 and 46 to complete the power circuit and power up the defibrillator 12 for use.

Figure 7:
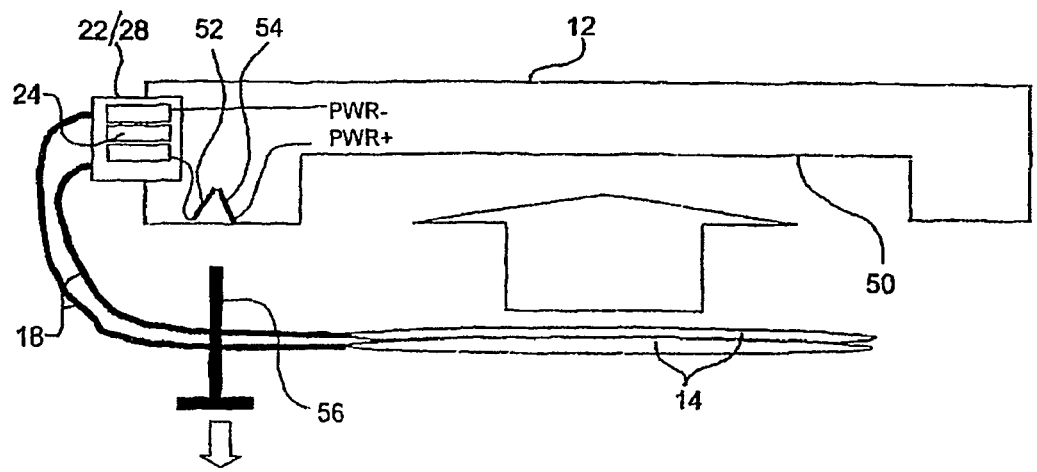

In the embodiment of FIG. 7, when the pads 14 are not in use they are stowed (attached, for example, by Velcro) in a shallow depression or recess 50 in the defibrillator 12 housing and the connectors 22 and 28 are pre-engaged (in FIG. 7 the two connectors are shown as a single item 22/28 for simplicity). In this case the batteries 24 are housed in the connector 22, as in FIG. 1. Within the defibrillator 12 the power supply circuit includes a pair of contacts 52 and 54 which are biased towards one another but normally held apart by an insulating pin 56 which is removably inserted into the defibrillator housing from outside. This pin 56 also cooperates with the pad leads 18 (or with the pads 14 themselves) such that when the pads 14 are removed from the recess 50 the pin 56 is automatically removed from between the contacts 52, 54 so that power from the batteries 24 is automatically connected to the defibrillator 12.

Figure 8:
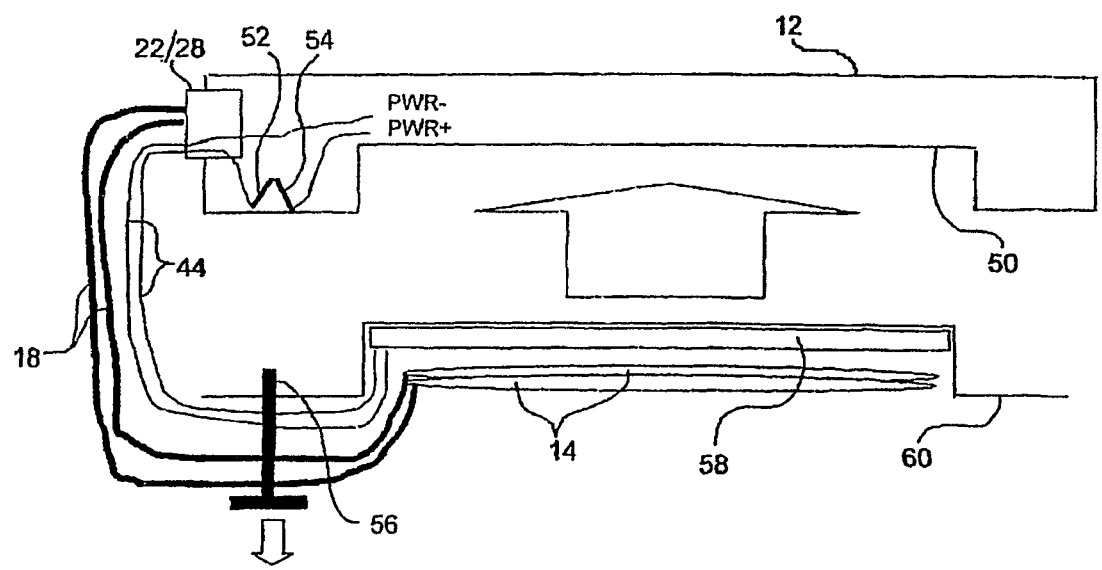

The embodiment of FIG. 8 is similar to that of FIG. 7 except that the batteries 24 are again no longer housed in the connector 22 but come in the form of a flat battery pack 58 housed, together with the pads 14, in a tray 60 which fits in the recess 50. In this case either the act of removing the pads from the tray, or the act of removing the tray, removes the pin 56 from between the power contacts 52, 54.

Figure 9:
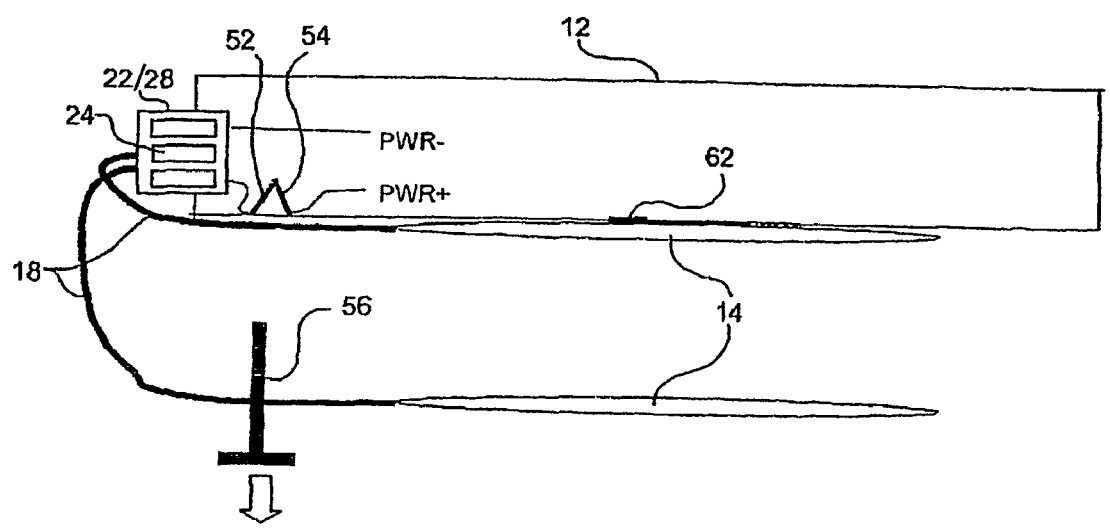

FIG. 9 shows a variation of FIG. 7 wherein one of the pads 14 is fixed to the rear of the defibrillator 12 housing and its electrical connection to the defibrillator is either made directly through the defibrillator housing via a contact 62 in the housing wall or via a lead 18 and the connectors 22/28 as in FIG. 7 (where the connection to the pad 14 is made directly via the contact 62 there will only need to be one terminal 20 on the connector 22 and correspondingly only one terminal 30 on the connector 28). In this embodiment the operation is similar to that of FIG. 7 except that the defibrillator 12 itself is placed on the patient's chest and effectively becomes one of the patient pads. The other pad 14 performs the device turn-on operation as by pulling out the mechanical block (pin 56) in the power supply circuit when it is pulled away from the defibrillator 12.

Figure 10:
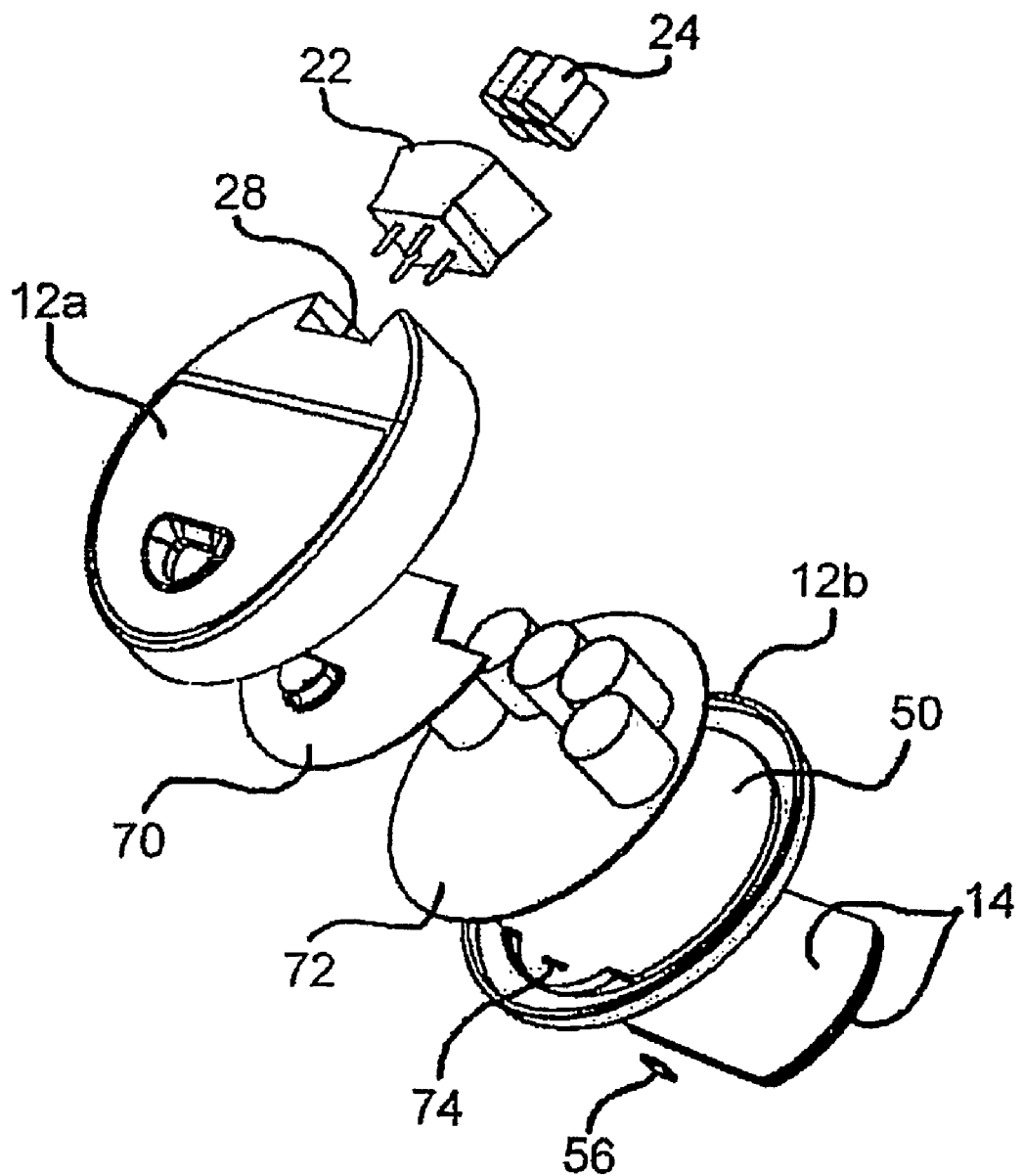
FIG. 10 is an exploded perspective view of a practical implementation of the embodiment of FIG. 7.
Figure 11:
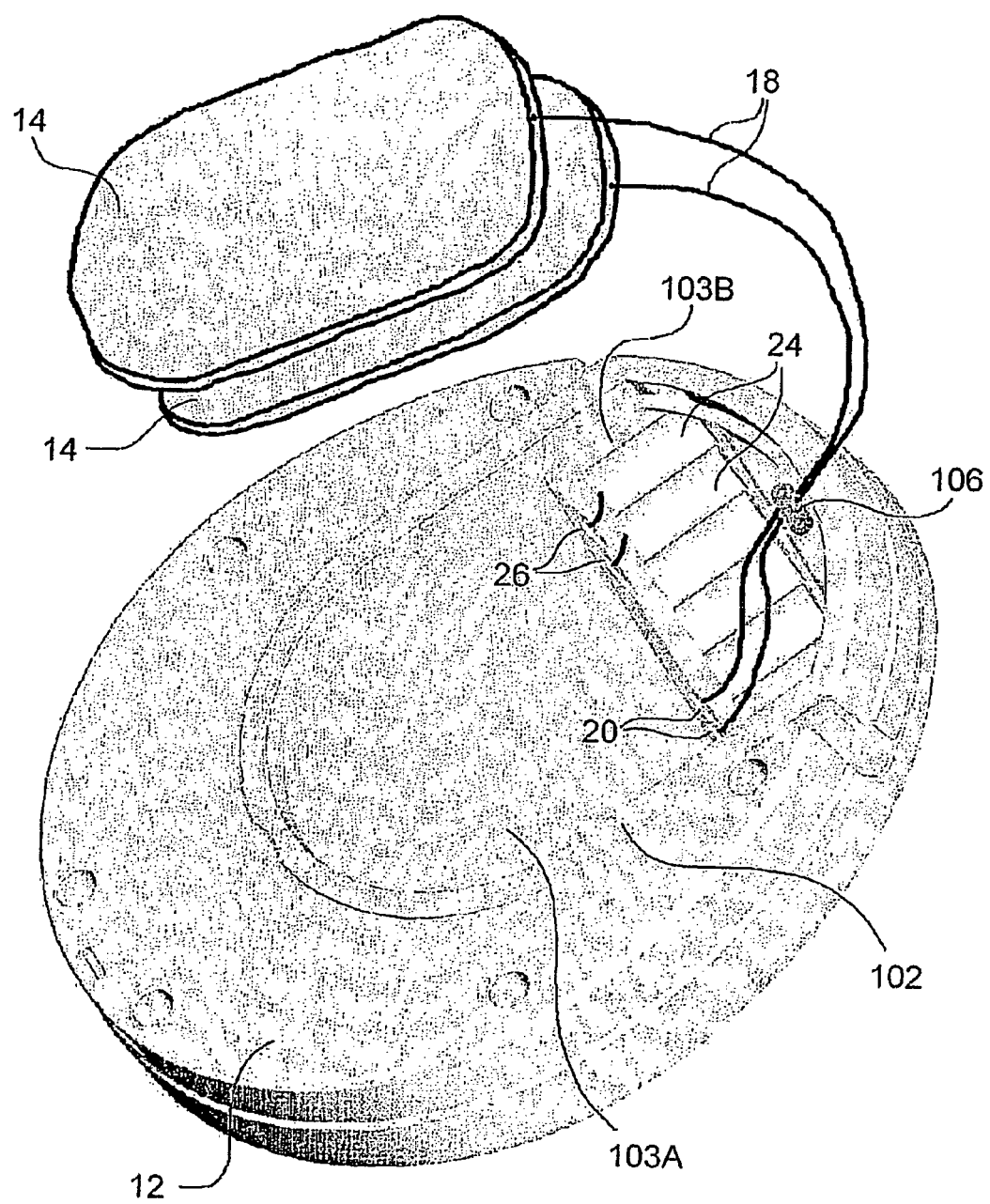
FIG. 11 is a top perspective view of a further embodiment of the invention.
Figure 12:
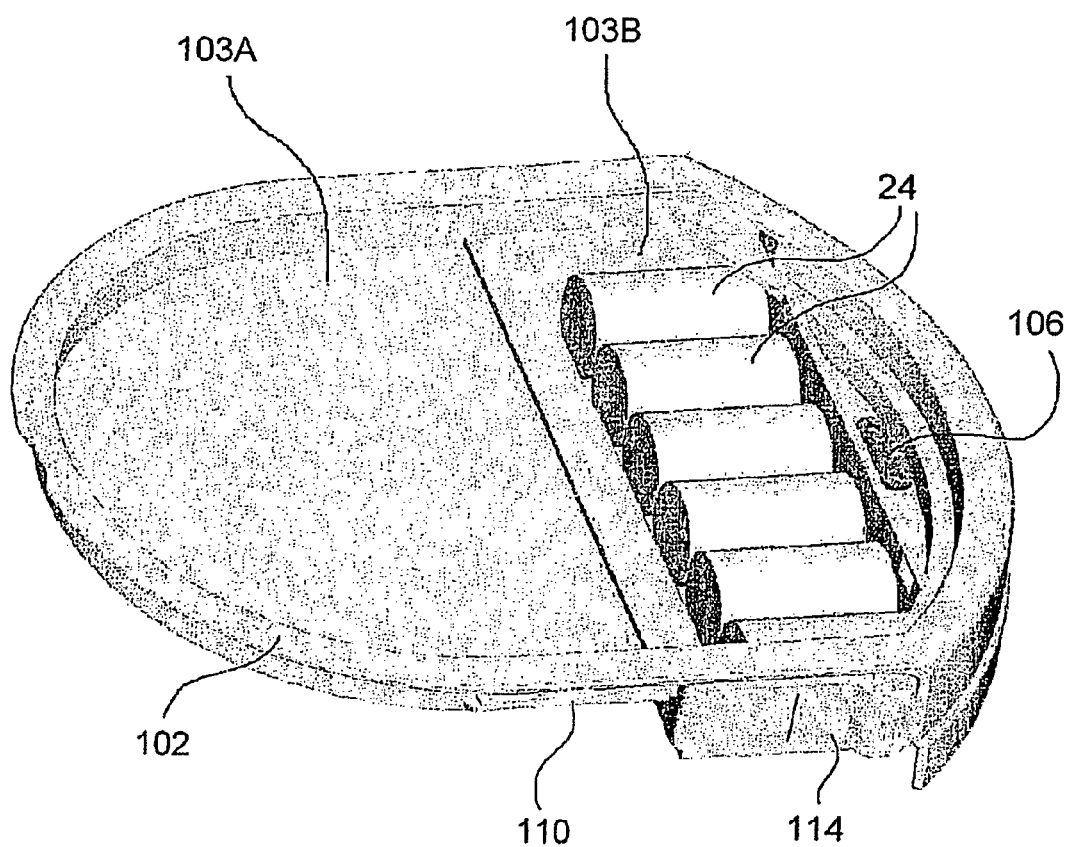
FIG. 12 is a top perspective view of the combined pad and battery housing of the embodiment of FIG. 11, omitting the pads.

FIG. 10 is an exploded perspective view of a practical implementation of the embodiment of FIG. 7 (the leads 18 are not shown). The defibrillator 12 comprises upper and lower housing halves 12a and 12b which contain a digital printed circuit board (PCB) 70 and a high voltage PCB 72. The batteries 24 are accommodated in the connector 22 which plugs into the socket connector 28 in the upper housing half 12a. The recess 50 is formed in the lower housing half 12b and contains the pads 14 when they are not in use. The insulating member 56 enters a slot 74 in the lower housing half 12b to be interposed between the contacts 52 and 54 (FIG. 7) and is operatively coupled to the pads 14 and/or their leads so that it is withdrawn from the slot 74 when the pads are removed from the recess 50.

Referring now to FIGS. 11 to 17, a further embodiment of the invention comprises a defibrillator 12 having a recess 100 (FIG. 15) to slidably receive a housing 102 which accommodates both the batteries 24 and the pads 14 in common and also functions as the connector 22.

Figure 13:
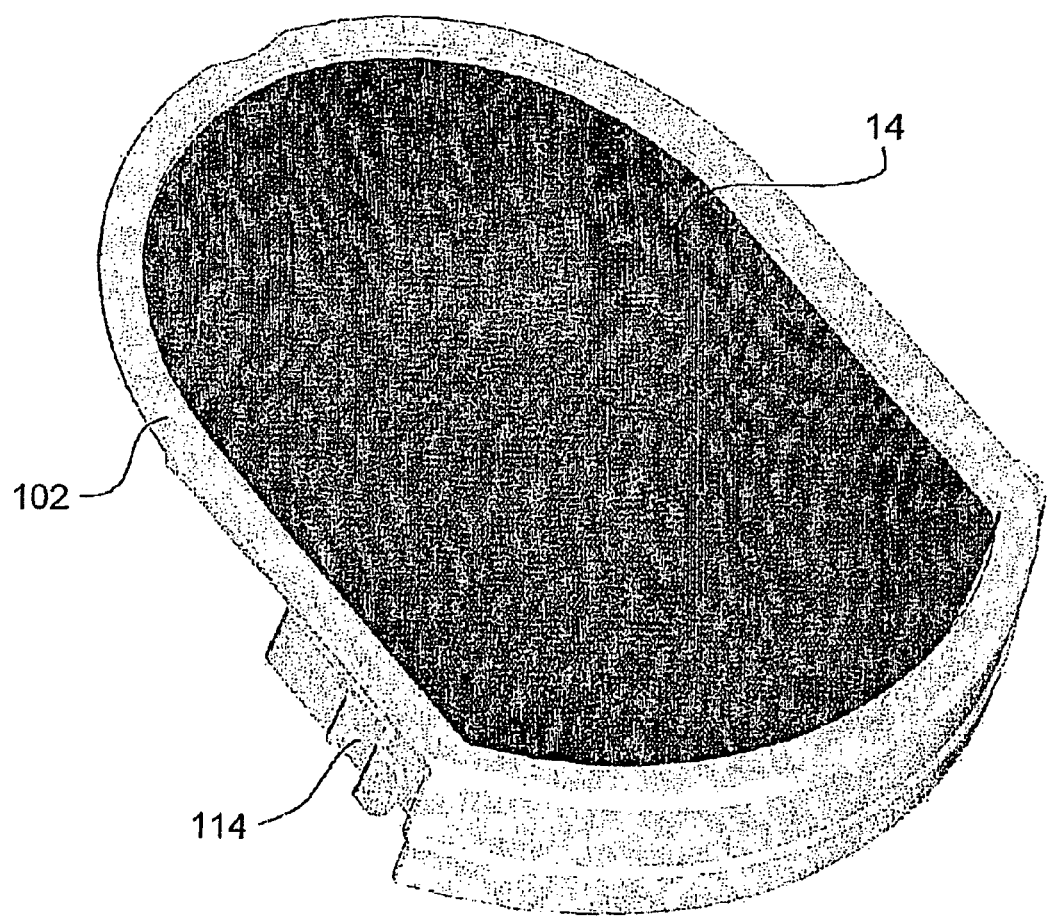
FIG. 13 is a top perspective view of the combined pad and battery housing of the embodiment of FIG. 11, including the pads.
Figure 14:
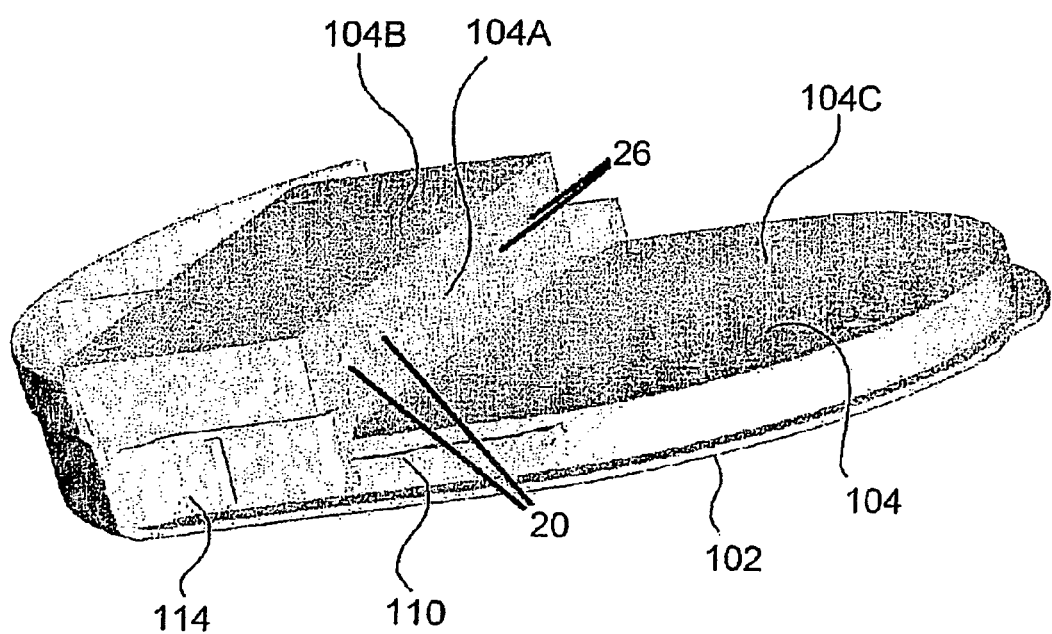
FIG. 14 is a perspective view of the underside of the combined pad and battery housing of the embodiment of FIG. 11.
Figure 17:
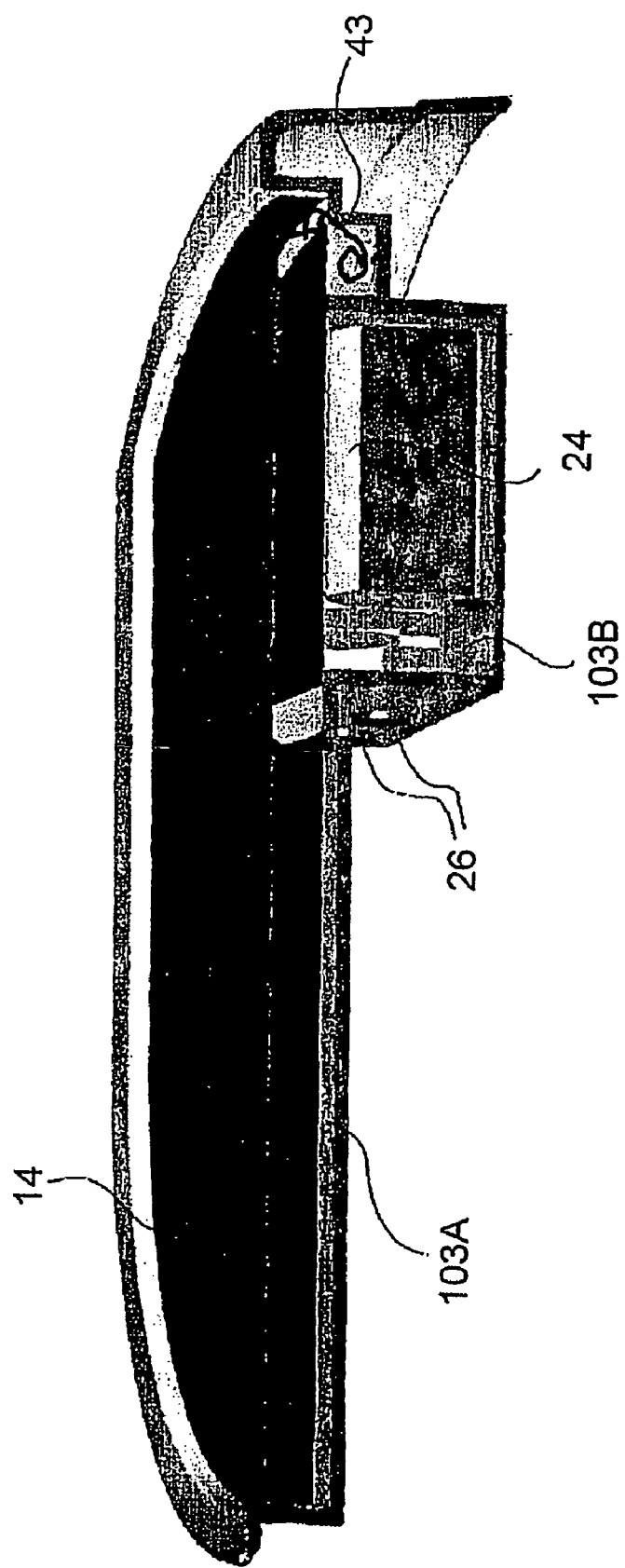
FIG. 17 is a cross-sectional view of the combined pad and battery housing of the embodiment of FIG. 11, including the pads.

The housing 102 comprises an upper shallow tray-like recess 103A for accommodating the pads 14 (as shown in FIGS. 13 and 17) and a deeper recess 103B occupying part of the area of the tray-like recess 103A for accommodating the batteries 24. Accordingly, the housing 102 has a stepped lower surface 104, FIG. 14, with a riser portion 104A joining the two portions 104B and 104C of the lower surface which correspond respectively to the tray-like and battery recesses 103A, 103B respectively and which are accordingly at different levels.

On the inside of the housing 102 the riser portion 104A has pairs of high voltage input and power output terminals 20, 26 respectively (FIG. 11), the pads 14 being connected to respective ones of the terminals 20 by respective leads 18 and the batteries 24 being connected in series across the terminals 26. The leads 18 pass under a strain relief member 106 to prevent strain on the connection between the leads 18 and terminals 20. The terminals 20, 26 pass fully through the wall of the housing 102 at the riser portion 104A to appear exposed at the lower surface 104, FIG. 14.

Figure 15:
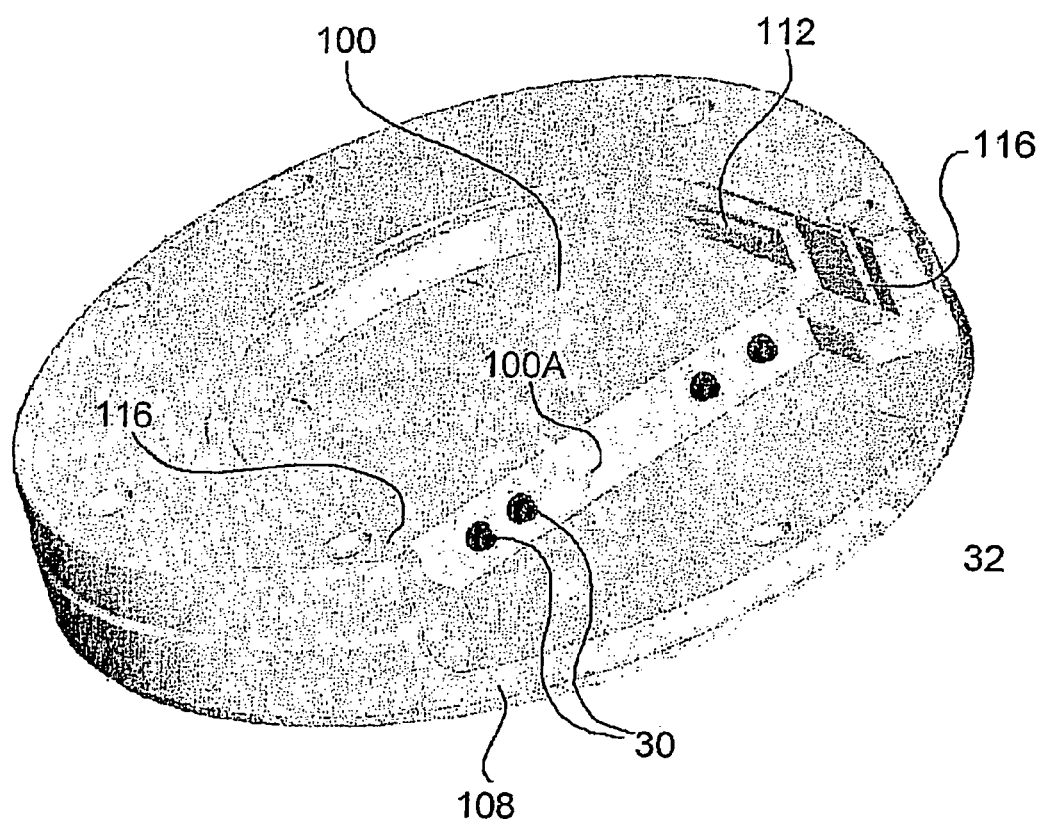
FIG. 15 is a top perspective view of the defibrillator to which the combined pad and battery housing is fitted.
Figure 16:
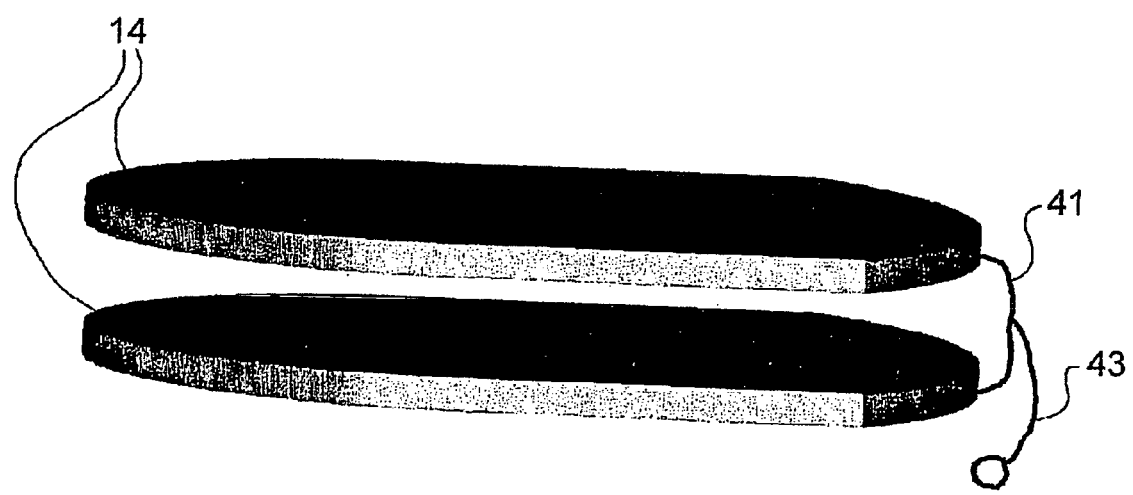
FIG. 16 shows the pads used in the embodiment of FIG. 11.

The recess 100 in the defibrillator 12, FIG. 15, has a stepped formation complementary to that of the housing 102, the recess 100 extending to the edge 108 of the defibrillator 12. The recess 100 has a riser portion 100A having pairs of terminals 30, 32 for mating with the corresponding pairs of terminals 20, 26 on the housing 102, the terminals 30,32 extending through the wall of the defibrillator housing at the riser portion 100A and being connected to the internal circuitry (not shown) of the defibrillator 12.

In use, the batteries 24 are inserted in the recess 103B of the housing 102 and then the pads 14 are laid in the shallow recess 103A over the batteries, FIG. 13. The leads 18 are neatly coiled up above the batteries 24. The pads are joined by a frangible link 41 (FIG. 16) as previously described, this being connected by a short piece of cord 43 to the strain relief member 106 (or elsewhere to the housing 102). The pads 14 are covered with a peel-off protective cover (not shown).

Now the housing 102 is slid into the recess 100 from the edge 108 of the defibrillator 12, the housing 102 being slid in a direction substantially parallel to the plane of the shallow recess 103A. The sliding movement is guided by ribs 110 on opposite sides of the housing 102 engaging under corresponding ribs 112 on opposite sides of the recess 100. When the housing 102 is fully home in the recess 100 resilient ears 114 on opposite sides of the housing 102 engage slots 116 on opposite sides of the recess 100, thereby retaining the housing 102 in position in the recess 100. In the fully home position the terminals 20, 26 exposed on the underside of the housing 102 (FIG. 14) mate with the terminals 30, 32 respectively on the defibrillator 12.

To use the defibrillator, the covering over the pads 14 is peeled off and the pads 14 removed from the recess 103A. This act of removal severs the frangible link 41 thus powering up the defibrillator 12 as previously described (alternatively the cord 43 may be omitted and the link 41 severed by separation of the pads 14). This is the situation shown in FIG. 11, where the pads 14 are shown deployed for use. After use, the housing 102 is removed from the defibrillator 12 by squeezing the ears 114 towards one another to disengage from the slots 116 and sliding the housing 102 out of the recess 100. Now a fresh housing 102 containing pads and batteries ready for the next use of the defibrillator is slid into the recess 100.

Figure 18:
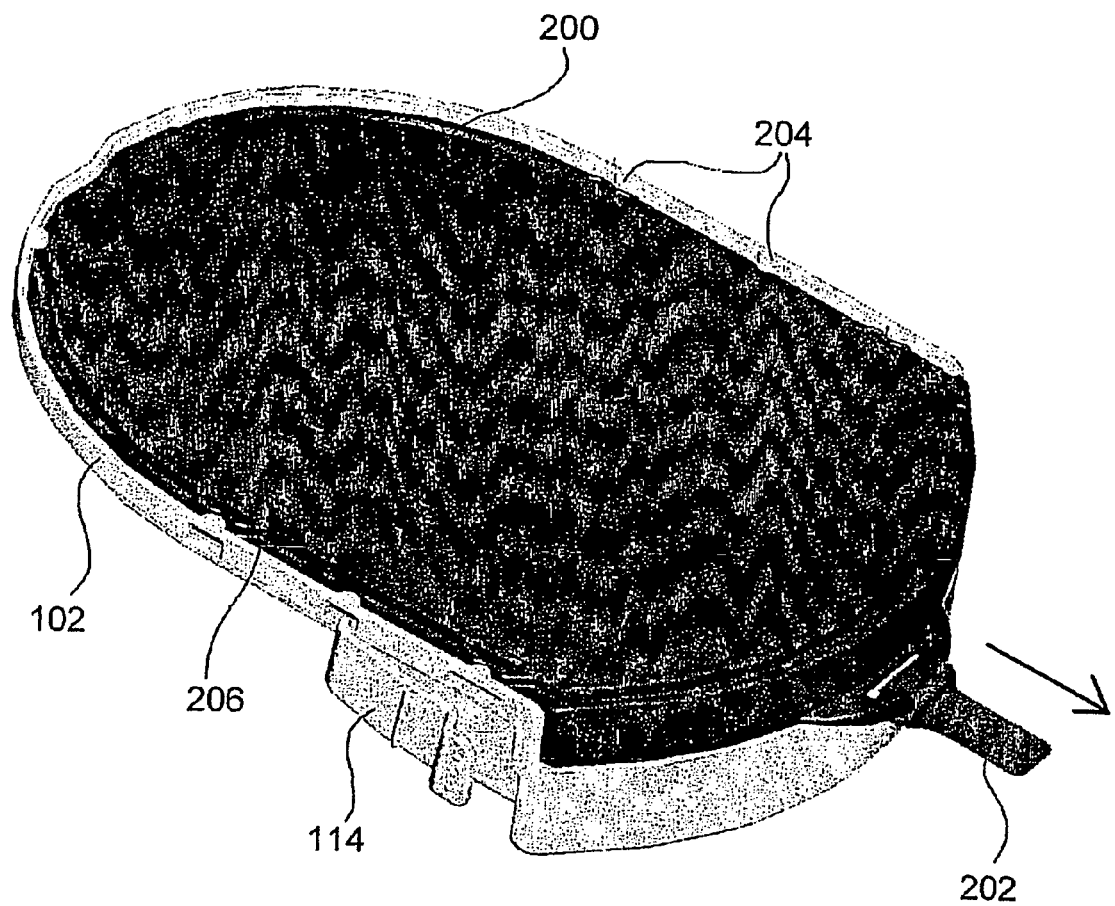
FIG. 18 is a top perspective view, similar to FIG. 13, of a combined pad and battery housing of a still further embodiment of the invention.
Figure 19:
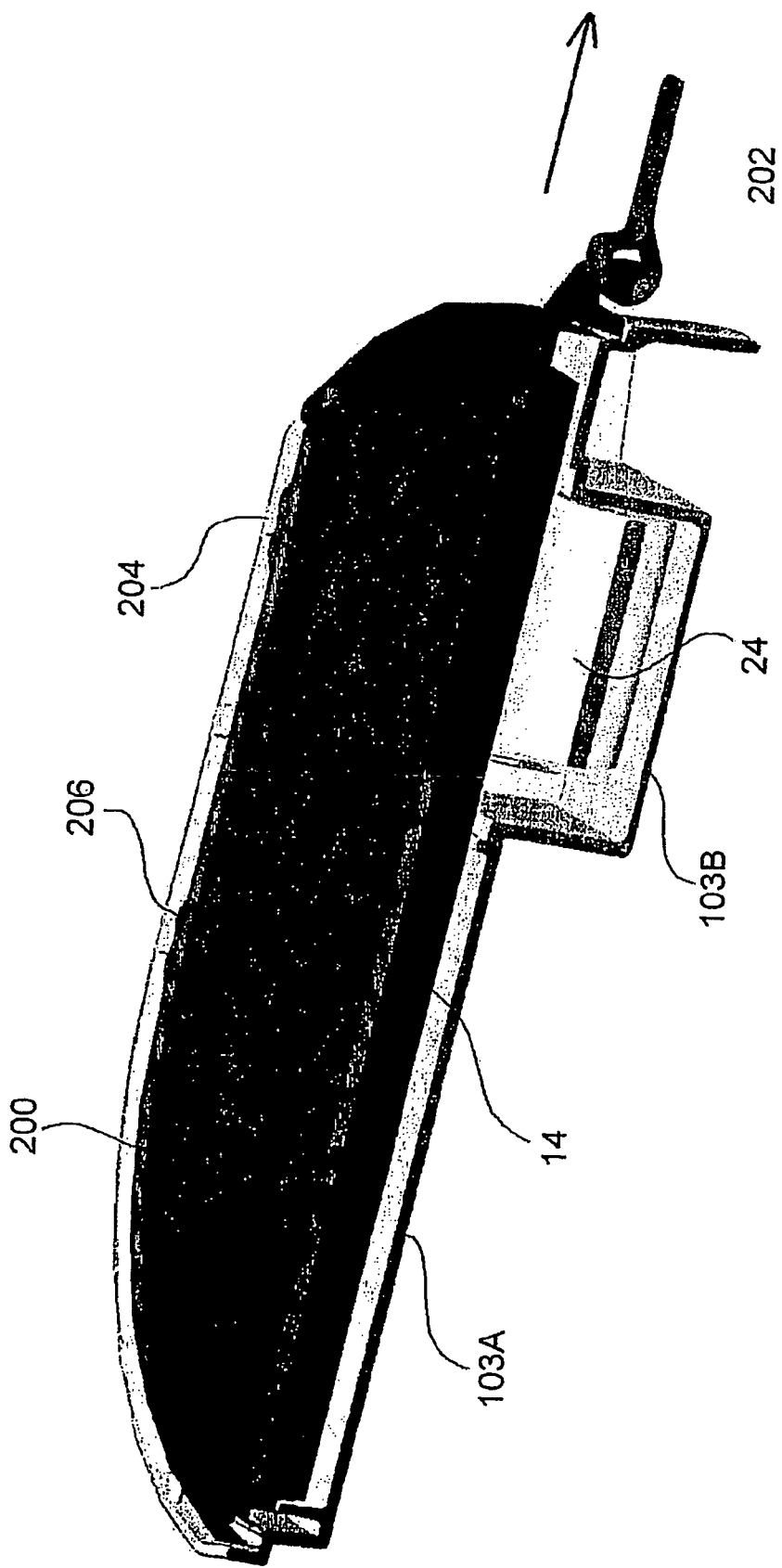
FIG. 19 is a cross-sectional view of the combined pad and battery housing of FIG. 18.

FIGS. 18 and 19 are views, similar to FIGS. 13 and 17, of a combined pad and battery housing of a still further embodiment of the invention. Since the main defibrillator body 12, as seen for example in FIG. 15, remains substantially unchanged in this embodiment, only the combined pad and battery housing 102 is shown. As before, the housing 102 is slid into the recess 100 from the edge 108 of the defibrillator 12 until the resilient ears 114 engage the slots 116 to retain the housing 102 in position in the recess 100 with the terminals 20, 26 mating with the terminals 30, 32 respectively.

However, in this embodiment the tray-like recess 103A is closed by a lid 200 which can be slid off the housing 102 in the direction of the arrow in FIGS. 18 and 19 by pulling on a tab 202 fixed to the front edge of the lid. The pads 14 are removably fitted to the underside of the lid 200, so that removal of the lid automatically removes the pads 14 from the recess 103A. The act of sliding the lid 200 out of the housing 102 automatically breaks the frangible link 43 (not shown in FIG. 19) to power up the device as previously described. The lid 200 is releasably retained in position on the housing 102 by integrally moulded pips 204 on the edge of the housing which resiliently engage respective shallow depressions 206 on the edge of the lid.

The invention is not limited to the embodiments described herein which may be modified or varied without departing from the scope of the invention.

The invention claimed is:

1. A portable defibrillator comprising a main housing containing defibrillator circuitry and a disposable sub-housing removably fitted to the main housing, the sub-housing comprising an electrode storage location containing a pair of defibrillator electrodes, at least one battery within said sub-housing for powering the defibrillator circuitry, and a connector for electrically connecting the sub-housing to the main housing, wherein the connector has power output terminals for connecting the at least one battery to the defibrillator circuitry and at least one high voltage input terminal for receiving a defibrillation voltage to be applied to the electrodes, wherein the electrodes are electrically connected by a frangible connection which is broken when the electrodes are deployed from the storage location, and wherein the defibrillator circuitry determines when the frangible connection is broken to complete a power circuit in the main housing for energizing the electrodes.

2. A defibrillator as claimed in claim 1, wherein the sub-housing is slidable into a complementary recess in the main housing, the sliding movement bringing the terminals on the the main housing and the sub-housing into engagement.

3. A defibrillator claimed in claim 2, wherein the sub-housing comprises a shallow upper tray-like recess for accommodating the defibrillator electrodes and a deeper battery-containing recess occupying part of the area of the tray-like recess, wherein the main housing has a stepped recess complementary to that of the lower surface of the sub-housing, wherein the sub-housing is slid into the recess in the main housing from an edge thereof in a direction substantially parallel to the plane of the tray-like recess, and wherein the engaging terminals are located on riser portions of the lower surface of the sub-housing and the complementary recess in the main housing.

4. A defibrillator as claimed in claim 1, wherein removing the electrodes from the storage location breaks the frangible connection.

5. A defibrillator as claimed in claim 1, wherein removing the electrodes from the stowage location and separating the electrodes for use breaks the frangible connection.

* * * * *